United States Patent [19]

Cragoe, Jr. et al.

[11] 4,342,776

[45] Aug. 3, 1982

[54] 4-SUBSTITUTED-3-HYDROXY-3-PYRROLINE-2,5-DIONE INHIBITORS OF GLYCOLIC ACID OXIDASE

[75] Inventors: Edward J. Cragoe, Jr., Lansdale; Clarence S. Rooney, Worcester, both of Pa.; Haydn W. R. Williams, Dollard des Ormeaux, Canada

[73] Assignee: Merck & Co., Inc., Rahway, N.J.

[21] Appl. No.: 91,294

[22] Filed: Nov. 5, 1979

[51] Int. Cl.³ .................. A61K 31/40; C07D 207/416
[52] U.S. Cl. .............................. 424/274; 260/326.5 C
[58] Field of Search .................. 260/326.5 C; 424/274

[56] References Cited
U.S. PATENT DOCUMENTS 3,340,263  9/1967  Stachelln et al. .

OTHER PUBLICATIONS

Liao et al., Arch. Biochem. Biophys., 154, pp. 68–75 (1973).
Harlay, J. Pharm. Chim., 24, pp. 537–548 (1936).
Randall et al., J. Med. Chem., 22, pp. 608–614 (1979).
G. S. Skinner et al., J. Am. Chem. Soc., 73, pp. 2230–2233 (1951) and 70, pp. 4011–4013 (1948).

*Primary Examiner*—David B. Springer
*Attorney, Agent, or Firm*—Raymond M. Speer; Michael C. Sudol, Jr.

[57] ABSTRACT

Novel 4-substituted-3-hydroxy-3-pyrroline-2,5-diones are disclosed which inhibit glycolic acid oxidase and thus are useful in the treatment and prevention of calcium oxalate kidney stone formation. A novel process for their preparation is also disclosed.

11 Claims, No Drawings

4-SUBSTITUTED-3-HYDROXY-3-PYRROLINE-2,5-DIONE INHIBITORS OF GLYCOLIC ACID OXIDASE

BACKGROUND OF THE INVENTION

Close to 70% of kidney stones in man are composed partially or predominantly of calcium oxalate. There is no satisfactory drug specific for the treatment of calcium oxalate renal lithiasis, nor for prophylactic use by patients prone to recurrent attacks of this disease.

The most common treatment for renal lithiasis due to calcium oxalate consists of surgical removal of stones, control of the diet to restrict calcium or oxalate, and ingestion of large quantities of water to dilute the urine. Attempts at chemotherapy have included the administration of magnesium oxide, calcium carbimide, orthophosphate, cellulose phosphate, isocarboxazide, thiazide diuretics, allopurinol and succinimide. Limited success has been realized by these drug approaches. No drug which specifically inhibits the biosynthetic formation of oxalic acid has previously been developed for the treatment of calcium oxalate renal lithiasis.

The immediate metabolic precursor of the majority of the oxalate in the urine of a typical patient is glyoxylic acid. In turn its most important precursor is glycolic acid. The enzyme glycolate oxidase is able to carry out the oxidation of glycolic acid, through glyoxylic acid, to oxalic acid. Inhibition of this enzyme will, therefore, reduce the concentration of oxalic acid in the kidney and bladder, decreasing the probability that calcium oxalate crystallization will occur. Thus inhibitors of glycolate oxidase provide a specific approach to the prevention and treatment of calcium oxalate renal lithiasis.

Liao, et al, *Arch. Biochem. Biophys.*, 154, 68–75 (1973) have shown that phenyllactic acid and n-heptanoic acid, which are inhibitors of glycolate oxidase, inhibit oxalate biosynthesis in isolated perfused rat liver. These compounds are not sufficiently potent to be useful as drugs.

The preparation of 3-hydroxy-4-phenyl-3-pyrroline-2,5-dione

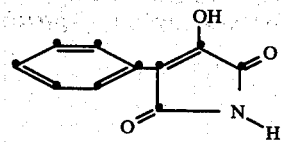

has been described by Harlay, *J. Pharm. Chim.*, 24, 537–48 (1936). 3-Hydroxy-4-aryl-3-pyrroline-2,5-diones are described in U.S. Pat. No. 3,349,263 as intermediates in the preparation of antiphlogistic substances. A number of 3-hydroxy-4-substitutedphenyl-3-pyrroline-2,5-diones are reported by G. S. Skinner, et al., *J. Am. Chem. Soc.*, 73, 2230 (1951). (In this paper these compounds are referred to as pyrrolidine-2,3,5-trione derivatives). 3-Hydroxy-4-(4-bromo-1-naphthyl)-3-pyrroline-2,5-dione is described by G. S. Skinner, et al., *J. Am. Chem. Soc.*, 70, 4011 (1948).

SUMMARY OF THE INVENTION

It has now been found that novel compounds of the formula:

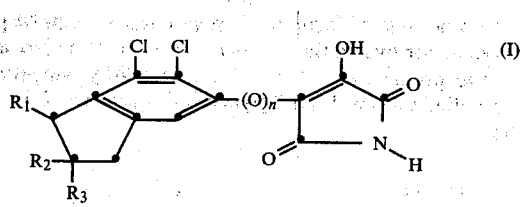

wherein
n is 0 or 1;
$R_1$ is —OH or =O;
$R_2$ is loweralkyl containing 1 to 3 carbons;
$R_3$ is loweralkyl containing 1 to 3 carbons, cyclolow-eralkyl containing 4 to 6 carbons, with the proviso that when n is 1, $R_1$ is not =O or a pharmaceutically acceptable salt thereof are potent inhibitors of glycolate oxidase. They are, therefore, useful in the treatment and prevention of calcium oxalate kidney and bladder stone formation.

DETAILED DESCRIPTION

About 70% of all renal calculi contain oxalate as the main component of the matrix. In the majority of patients the condition is associated with a higher than average level of metabolically produced oxalate. The major pathway for biosynthesis of oxalate can be represented as follows:

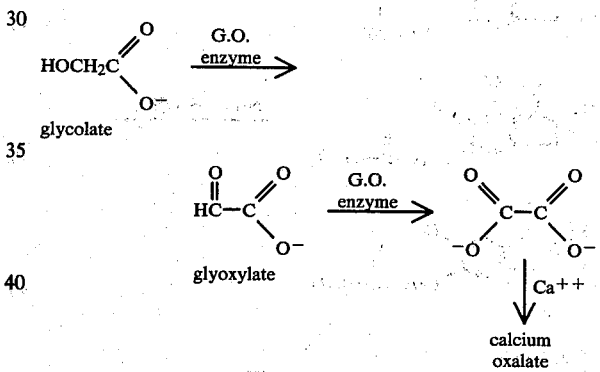

Glyoxylate is the major immediate forerunner of oxalate. An inhibitor of glycolate oxidase (G.O.) will inhibit both the conversion of glyoxylate to oxalate as well as the production of glyoxylate from glycolate. By reducing oxalic acid levels in the urine with the compounds of this invention, the formation of oxalate calculi will be reduced or prevented.

Compounds of formula (I) are potent inhibitors of glycolate oxidase and thus are useful in restricting oxalate levels in the blood and urine. Further, they are useful in the treatment and prevention of renal disease due to calcium oxalate stone formation in the kidney and bladder. They may also be useful in the treatment of the genetically inherited diseases termed Hyperoxaluria types I and II.

Compounds of formula (I) have been unexpectedly found to block the contractions of guinea pig ileum induced by Slow Reacting Substance of Anaphylaxis (SRS-A). They are ineffective against contractions caused by histamine, which demonstrates specificity against SRS-A. SRS-A is considered a major mediator in human allergic asthma. Thus the compounds of formula (I) are useful in the treatment of allergy, especially allergic asthma.

Compounds of formula (I) wherein n=o can be prepared according to the following novel route illustrated by the preparation of 4-(6,7-dichloro-2-cyclopentyl-2-methylindan-1-on-5-yl)-3-hydroxy-3-pyrroline-2,5-dione.

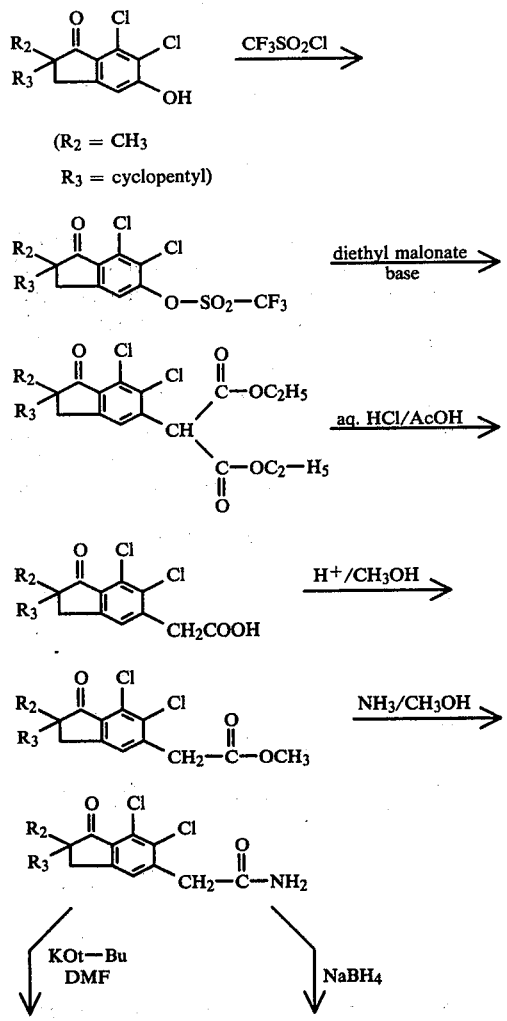

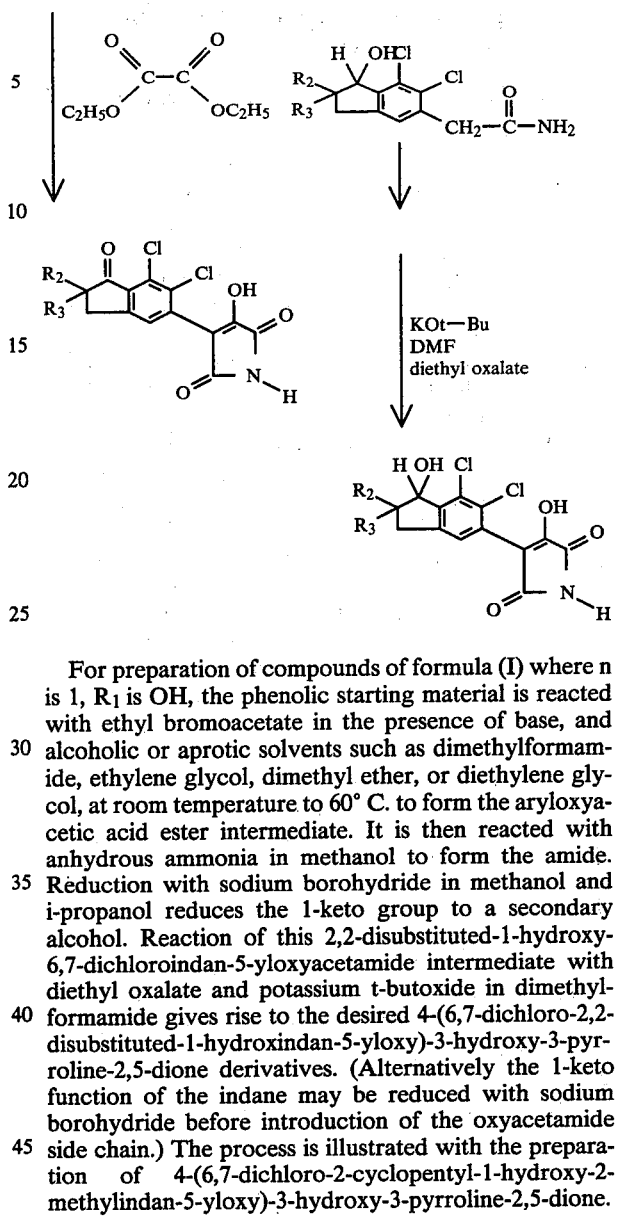

For preparation of compounds of formula (I) where n is 1, $R_1$ is OH, the phenolic starting material is reacted with ethyl bromoacetate in the presence of base, and alcoholic or aprotic solvents such as dimethylformamide, ethylene glycol, dimethyl ether, or diethylene glycol, at room temperature to 60° C. to form the aryloxyacetic acid ester intermediate. It is then reacted with anhydrous ammonia in methanol to form the amide. Reduction with sodium borohydride in methanol and i-propanol reduces the 1-keto group to a secondary alcohol. Reaction of this 2,2-disubstituted-1-hydroxy-6,7-dichloroindan-5-yloxyacetamide intermediate with diethyl oxalate and potassium t-butoxide in dimethylformamide gives rise to the desired 4-(6,7-dichloro-2,2-disubstituted-1-hydroxindan-5-yloxy)-3-hydroxy-3-pyrroline-2,5-dione derivatives. (Alternatively the 1-keto function of the indane may be reduced with sodium borohydride before introduction of the oxyacetamide side chain.) The process is illustrated with the preparation of 4-(6,7-dichloro-2-cyclopentyl-1-hydroxy-2-methylindan-5-yloxy)-3-hydroxy-3-pyrroline-2,5-dione.

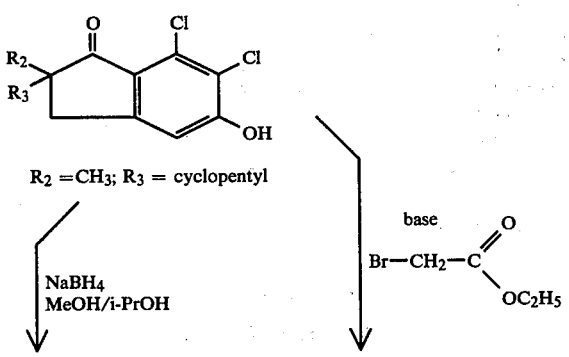

$R_2$ =$CH_3$; $R_3$ = cyclopentyl

-continued

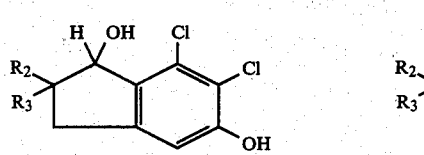 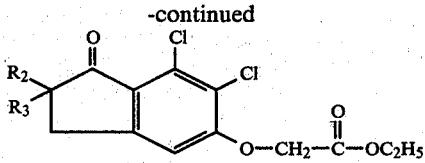

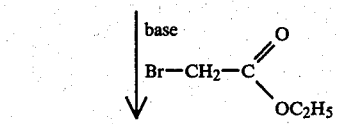

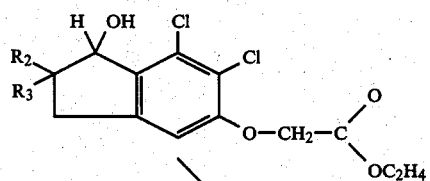 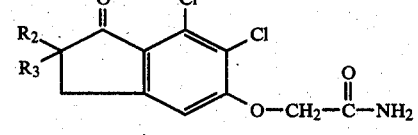

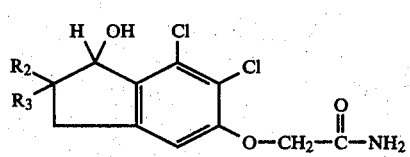

Kot—Bu
DMF
Diethyl malonate

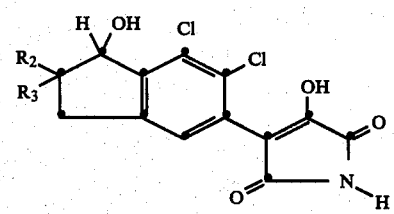

The following examples, given by way of illustration and not to be construed as limiting, further clarify the invention.

General Procedure for the Preparation of Methyl Substituted Indanylacetates

In this novel procedure the indanyl triflate ester is prepared by reaction of the appropriate 5-hydroxyindane starting material and trifluoromethanesulfonyl chloride. The triflate substituent is displaced by interaction with the carbanion derived from diethyl malonate to give a 2-(indanyl substituted) diethyl malonate. Ester hydrolysis and decarboxylation in a hot mixture of hydrochloric acid and acetic acids converts this intermediate to the 2-(5-indanyl)acetic acid. The indanylacetic acid intermediate is converted to the methyl ester by reaction with methanolic hydrogen chloride. The 1-oxo-2,2-disubstituted-5-hydroxy-6,7-dichloroindanes required as starting materials in these examples are prepared as described by O. W. Woltersdorf, Jr., S. J. deSolms, E. M. Schultz, and E. J. Cragoe, Jr., *J. Med. Chem.* 20, 1400 (1977).

EXAMPLE 1

Preparation of 6,7-Dichloro-2-cyclopentyl-2-methyl-1-oxoindan-5-yl Trifluoromethylsulfonate A mixture of 6,7-dichloro-2-cyclopentyl-2-methyl-5-hydroxy-1-indanone (20.93 g, 0.07 mole), anhydrous potassium carbonate (25.95 g, 0.188 mole) and dry acetone (350 ml) was stirred at room temperature and treated with trifluoromethanesulphonyl chloride (12.70 g, 0.0754 mole) in portions. Reaction was monitored by thin layer chromatography and was complete about 15 minutes after the termination of the addition. The mixture was filtered and evaporated to dryness. The residue was dissolved in methylene chloride, the solution dried (MgSO$_4$) and evaporated under vacuum to an oil. Final evaporation was at ~50° C./0.05 Torr giving 28.45 g (94%) of product. IR $\nu$ max KBr 2945, 2860, 1720, 1430 cm$^{-1}$; NMR $\delta$ CDCl$_3$; 7.42 (s, 1H, aromatic H); 3.15 and 2.77 (2 d, 2×1H, J=18 Hz, benzylic CH$_2$), ~2.5-1 (m, 9H, cyclopentyl H), 1.23 (s, 3H, CH$_3$).

Elemental analysis for C$_{16}$H$_{15}$Cl$_2$F$_3$O$_4$S; Required: C, 44.56; H, 3.51; S, 7.43; Found: C, 45.31; H, 3.59; S, 6.96.

EXAMPLE 2

Preparation of Diethyl 2-(6,7-Dichloro-2-cyclopentyl-2-methyl-1-oxoindan-5-yl) Malonate To a stirred suspension of sodium hydride (2.88 g, 120 mmole) in dry dimethylformamide (20 ml) under dry nitrogen and cooled in an ice-bath was added dropwise a solution of diethyl malonate (19.2 g, 120 mmole) in dimethylformamide (30 ml). The mixture was stirred for 1 hour in an ice-bath and another hour at room temperature. Then it was cooled in an ice-bath again and 6,7-dichloro-2-cyclopentyl-2-methyl-1-oxoindan-5-yl trifluoromethylsulfonate (12.93 g, 30 mmole), prepared by the process of Example 1, in dimethylformamide (25 ml) was added dropwise over 1½ hours. The mixture was stirred at room temperature overnight and then poured into a mixture of ice-water (750 ml), methylene chloride (200 ml) and 6 N hydrochloric acid (20 ml). The methylene chloride layer was separated and the aqueous layer extracted with methylene chloride (50 ml). The combined extract was washed with water (500 ml), dried with anhydrous $MgSO_4$ and evaporated under vacuum, and finally at $\sim 70°$ C./0.05 Torr, to give an oil (18.28 g). This was purified by chromatography on Merck silica gel (1.04 kg) using 1,1,1-trichloroethane as the solvent. The product was accompanied by some diethyl malonate which was removed at 125° C./0.05 Torr to give a viscous oil, 10.25 g (77%). IR $\nu$ max KBr 2945, 2860, 1749, 1732, 1720, 1300; NMR $\delta$ ($CDCl_3$) 7.52 (s, 1H, aromatic H), 5.30 (s, 1H, COCHCO), 4.30 (q, 4H, J=8 Hz, 2×$OCH_2$), 3.13 and 2.91 (2×d, 2×1H, J=18 Hz, benzylic $CH_2$), ~1.8–0.9 (m, 9H, cyclopentyl), 1.33 (t, 6H, J=8 Hz, 2×$CH_3$), 1.26 (s, 3H, $CH_3$).

Elemental Analysis for $C_{22}H_{26}Cl_2O_5$; Required: C, 59.87; H, 5.94; Cl, 16.06; Found: C, 59.87; H, 6.00; Cl, 15.85.

EXAMPLE 3

Preparation of 6,7-Dichloro-2-cyclopentyl-2-methyl-1-oxoindan-5-ylacetic Acid A mixture of the diethyl indanylmalonate (5.00 g, 11.34 mmole), prepared by the process set forth in Example 2, ~9 N hydrochloric acid (5 ml) and acetic acid (50 ml) was heated in an oil bath at 125° C. for 55 hours. The mixture was evaporated under reduced pressure and the syrupy residue was dissolved in methylene chloride (50 ml). The solution was washed with water (4×25 ml), dried with anhydrous $MgSO_4$ and evaporated under vacuum to a foam. The acid was used without further purification for the next step in the synthesis but a portion was characterized as the dicyclohexylamine salt, mp 167°–167.5° C. (dec) (from acetonitrile).

Elemental Anal. for $C_{17}H_{18}Cl_2O_3.C_{12}H_{23}N$; Required: C, 66.66; H, 7.91; N, 2.68 Found: C, 66.70; H, 8.13; N, 2.62.

EXAMPLE 4

Preparation of Methyl 6,7-Dichloro-2-cyclopentyl-2-methyl-1-oxoindan-5-ylacetate Acetyl chloride (20 ml) was added slowly to ice-cold methanol (50 ml) and the resulting mixture was added to the indanylacetic acid as prepared in Example 3 above. The mixture was allowed to stand for 24 hours, then it was evaporated under reduced pressure. The residue was dissolved in methylene chloride (50 ml) and the solution was washed with water (2×10 ml), dried with anhydrous $MgSO_4$ and evaporated in vacuo to a pale amber oil, finally finally at 100° C./0.05 Torr to yield 4.09 g of product (theory 4.03 g). IR $\nu$ max KBr 2945, 2860, 1737, 1713; NMR $\delta$ ($CDCl_3$) 7.34 (s, 1H, aromatic H), 3.91 (s, 2H, $CH_2CO$), 3.73 (s, 3H, $OCH_3$), 3.10 and 2.70 (2×d, 2×1H, benzylic $CH_2$), ~1.8-0.9 (m, 9H, cyclopentyl), 1.22 (s, 3H, $CH_3$).

When the sequence of reactions of Example 1 to 4 is applied to 6,7-dichloro-5-hydroxy-2-(i-propyl)-2-methyl-1-oxoindane as starting material, there is obtained methyl 6,7-dichloro-2-(i-propyl)-2-methyl-1-oxoindan-5-ylacetate.

When 6,7-dichloro-2-ethyl-5-hydroxy-2-methyl-1-oxoindane is utilized as starting material there is obtained methyl 6,7-dichloro-2-ethyl-2-methyl-1-oxoindan-5-ylacetate. When 6,7-dichloro-2-ethyl-5-hydroxy-2-(n-propyl)-1-oxoindane is employed as starting material, there is produced methyl 6,7-dichloro-2-ethyl-2-(n-propyl)-1-oxoindan-5-ylacetate.

When the procedure of Example 4 is applied to 6,7-dichloro-2,2-dimethyl-1-oxoindan-5-yloxyacetic acid, 6,7-dichloro-2-methyl-2-(i-propyl)-1-oxoindan-5-yloxyacetic acid, and 6,7-dichloro-2-methyl-2-cyclopentyl-1-oxoindan-5-yloxyacetic acid, there are obtained the corresponding methyl esters.

General Procedure for the Preparation of Indanyloxyacetic Acid Ethyl (or Methyl) Esters from Hydroxyindane Intermediates A general procedure for the preparation of indanyloxyacetic acid esters is as follows:

The hydroxyindane intermediate (10 mmole) is added to a solution of sodium (10 mmole) in ethanol (20 ml.) (i.e. sodium ethoxide) under nitrogen. To the cooled mixture is added ethyl (or methyl)bromoacetate (10 mmole) in ethanol (10 ml.) and then the mixture is stirred for up to twelve hours at room temperature. The ester is isolated by addition of water and extraction with methylene chloride. The crude ester obtained on evaporation of the methylene chloride is, in general, sufficiently pure to be used in the amide forming step.

Examples of indanyloxyacetic acid esters which are prepared by the above procedure are ethyl 6,7-dichloro-2-cyclopentyl-2-methyl-1-oxoindan-5-yloxyacetate, methyl 6,7-dichloro-1-hydroxy-2-methyl-2-(i-propyl)indan-5-yloxyacetate, and ethyl 6,7-dichloro-2-ethyl-1-hydroxy-2-(n-propyl)indan-5-yloxyacetate.

General Procedure for Preparing Substituted Acetamides

The substituted acetic acid esters and oxyacetic acid esters were converted to the corresponding amides by treatment with 7½ parts volume by weight of a saturated solution of ammonia in methanol at room temperature. Conversion to the amide was followed by thin layer chromatography. Examples of two substituted acetamides prepared by this process are set forth in Table II below.

In the case of 6,7-dichloro-2-cyclopentyl-2-methylindan-1-on-5-yloxyacetamide, solvates with a number of different solvents were formed. The solvate with formic acid was microanalyzed. The hemi-toluene solvate, $C_{17}H_{19}Cl_2NO_3.\frac{1}{2}C_6H_5CH_3$, mp 103°–110° C. was used for preparative purposes.

When the above procedure is applied to methyl 6,7-dichloro-2-(i-propyl)-2-methyl-1-oxoindan-5-ylacetate, methyl 6,7-dichloro-2-ethyl-2-methyl-1-oxoindan-5-ylacetate, and methyl 6,7-dichloro-2-ethyl-2-(n-propyl)-1-oxoindan-5-ylacetate, there are obtained 6,7-dichloro-2-(i-propyl)-2-methyl-1-oxoindan-5-ylacetamide, 6,7-dichloro-2-ethyl-2-methyl-1-oxoindan-5-ylacetamide, and 6,7-dichloro-2-ethyl-2-(n-propyl)-1-oxoindan-5-ylacetamide.

EXAMPLE 5

Preparation of 6,7-Dichloro-2-cyclopentyl-1-hydroxy-2-methylindan-5-yloxyacetamide 6,7-Dichloro-2-cyclopentyl-2-methyl-1-oxo-indan-5-yloxyacetamide hemi-toluene solvate (5.85 g, 14.55 mmole) was added to a mixture of isopropanol (75 ml) and methanol (15 ml). Sodium borohydride (553 mg,

TABLE II

| Compound | Yield % | MP °C. Solvent | Formula | Analysis Req. | Fd. |
|---|---|---|---|---|---|
| 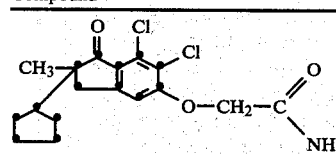 6,7-dichloro-2-cyclopentyl-2-methylindan-1-on-5-yloxyacetamide | 92 | 112–113 | $C_{17}H_{19}Cl_2NO_3$, HCOOH | C 53.74<br>H 5.26<br>N 3.48 | 53.83<br>5.49<br>3.12 |
| 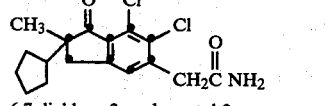 6,7-dichloro-2-cyclopentyl-2-methylindan-1-on-5-ylacetamide | 96 | (isolated as a foam) | $C_{17}H_{19}Cl_2NO_2$ | C 60.01<br>H 5.63<br>N 4.12 | 59.99<br>6.03<br>3.98 |

When the above procedure is applied to methyl 6,7-dichloro-2,2-dimethyl-1-oxoindan-5-yloxyacetate, methyl 6,7-dichloro-2-methyl-2-(i-propyl)-1-oxoindan-5-yloxyacetate and methyl 6,7-dichloro-2-methyl-2-cyclopentyl-1-oxoindan-5-yloxyacetic acid, there are obtained 6,7-dichloro-2,2-dimethyl-1-oxoindan-5-yloxyacetamide, 6,7-dichloro-2-methyl-2-(i-propyl)-1-oxoindan-5-yloxyacetamide and 6,7-dichloro-2-methyl-2-cyclopentyl-1-oxoindan-5-yloxyacetamide.

When the above procedure is applied to methyl 6,7-dichloro-1-hydroxy-2-methyl-2-(i-propyl)indan-5-yloxyacetate and ethyl 6,7-dichloro-2-ethyl-1-hydroxy-2-(n-propyl)indan-5-yloxyacetate there are obtained 6,7-dichloro-1-hydroxy-2-methyl-2-(i-propyl)indan-5-yloxyacetamide and 6,7-dichloro-2-ethyl-1-hydroxy-2-(n-propyl)indan-5-yloxyacetamide.

The amide, 6,7-dichloro-2-cyclopentyl-1-hydroxy-2-methylindan-5-yloxyacetamide, was prepared by the following alternate route, which is applicable for all compounds of this invention wherein $R_1$ is -OH.

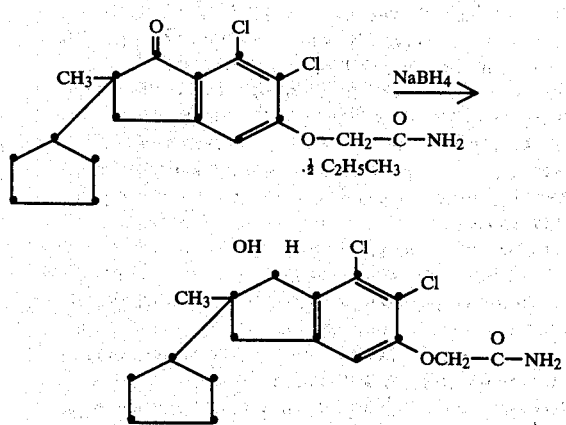

14.55 mmole) was added to the stirred mixture at room temperature. After 1 hour, a second portion of sodium borohydride (553 mg, 14.55 mmole) was added. After a further 3 hours, the reaction mixture was diluted with ice-water (250 ml) and extracted with ethyl acetate (2×100 ml). The extract was washed with water (250 ml) and then with saturated sodium chloride solution (50 ml) before drying over anhydrous magnesium sulphate. Evaporation of the solvent and recrystallization of the residue from acetonitrile gave the product as a mixture of the two racemates. mp 168°–179° C.

Anal. for $C_{17}H_{21}Cl_2NO_3$: Calc.: C, 56.99; H, 5.91; N, 3.91: Found: C, 57.08; H, 5.61; N, 3.89.

When 6,7-dichloro-2,2-dimethyl-1-oxoindan-5-yloxyacetamide and 6,7-dichloro-2-methyl-2-(i-propyl)-1-oxoindan-5-yloxyacetamide are treated as described in Example 5, there are obtained 6,7-dichloro-2,2-dimethyl-1-hydroxyindan-5-yloxyacetamide and 6,7-dichloro-2-methyl-2-(i-propyl)-1-hydroxyindan-5-yloxyacetamide respectively.

When 6,7-dichloro-2-(i-propyl)-2-methyl-1-oxoindan-5-ylacetamide, 6,7-dichloro-2-ethyl-2-methyl-1-oxoindan-5-ylacetamide, and 6,7-dichloro-2-ethyl-2-(i-propyl)-1-oxoindan-5-ylacetamide are treated as described in Example 5, there are obtained 6,7-dichloro-2-(i-propyl)-2-methyl-1-hydroxyindan-5-ylacetamide, 6,7-dichloro-2-ethyl-2-methyl-1-hydroxyindan-5-ylacetamide and 6,7-dichloro-2-ethyl-2-(n-propyl)-1-hydroxyindan-5-ylacetamide.

EXAMPLE 6

General Method for the Preparation of 3-Hydroxy-4-substituted-3-pyrroline-2,5-diones A mixture of the substituted acetamide, or oxyacetamide (10 mmole), diethyl oxalate (1.533 g, 10.5 mmole) and dry dimethylformamide (20 ml) is stirred under nitrogen or argon and cooled in an ice-bath. Potassium t-butoxide (2.464 g, 22 mmole) is added in two equal portions 15 minutes apart and the reaction mixture is stirred for about 30 minutes in the ice-bath and then at room temperature overnight. The reaction mixture is poured into ice-water (100 ml). If the potassium salt of the product dissolves, the aqueous mixture is extracted with ethyl acetate (2×35 ml) and then acidified with 6 N hydrochloric acid in order to precipitate the product. The product is either collected by filtration or by extraction with ethyl acetate.

If the potassium salt is not soluble when the reaction mixture is quenched in ice-water, then it is necessary to acidify the resulting suspension and collect the product by filtration. The crude product is generally less pure when obtained in this way.

The compounds may be solvated after recrystallization (with either DMF, dioxane, isopropanol or acetonitrile) and require drying at 110° C./0.05 Torr in order to remove the solvate.

Examples of 3-hydroxy-4-substituted-3-pyrroline-2,5-diones prepared by this process are set forth in Table III below:

1-hydroxyindan-5-yloxyacetamide are utilized as starting materials in the reaction with diethyloxalate/potassium t-butoxide there are obtained 4-(6,7-dichloro-2,2-dimethyl-1-hydroxyindan-5-yloxy)-3-hydroxy-3-pyrroline-2,5-dione and 4-(6,7-dichloro-2-methyl-2-(i-propyl)-1-hydroxyindan-5-yloxy)-3-hydroxy-3-pyrroline-2,5-dione.

When 6,7-dichloro-2-(i-propyl)-2-methyl-1-hydroxyindan-5-ylacetamide, 6,7-dichloro-2-ethyl-2-methyl-1-hydroxyindan-5-ylacetamide, and 6,7-dichloro-2-ethyl-2-(n-propyl)-1-hydroxyindan-5-ylacetamide are utilized as starting materials in the diethyloxalate/potassium t-butoxide reaction there are obtained 4-[6,7-dichloro-2-(i-propyl)-2-methyl-1-hydroxyindan-5-yl]-3-hydroxy-3-pyrroline-2,5-dione, 4-(6,7-dichloro-2-ethyl-2-methyl-1-hydroxyindan-5-yl)-3-hydroxy-3-pyrroline-2,5-dione, and 4-[6,7-dichloro-2-ethyl-2-(n-propyl)-1-hydroxyindan-5-yl]-3-hydroxy-3-pyrroline-2,5-dione.

Included within the scope of the invention are the

TABLE III

| Compound | Yield % | MP °C. Solvent | Formula | Analysis Req. | Fd. |
|---|---|---|---|---|---|
| 4-(6,7-dichloro-2-cyclopentyl-2-methylindan-1-on-5-yl)-3-hydroxy-3-pyrroline-2,5-dione N-methylpiperazine salt* | 58 | 213.5–214 dec. DMF/MeCN | $C_{19}H_{17}Cl_2NO_4$. $C_5H_{12}N_2$ | C 58.30 H 5.91 N 8.50 | 58.25 6.17 8.59 |
| 4-(6,7-dichloro-2-cyclopentyl-1-hydroxy-2-methylindan-5-yloxy)-3-hydroxy-3-pyrroline-2,5-dione dicyclohexylammonium salt* | 67 | 260–261 dec. DMF/MeCN | $C_{19}H_{19}Cl_2NO_5$. $C_{12}H_{23}N$ | C 62.73 H 7.1 N 4.72 | 62.99 7.63 5.03 |

*The hydroxypyrroline diones of this invention can also be named as 3-(substituted cudamyl)-4-hydroxy-3-pyrroline-2,5-diones.

When 6,7-dichloro-2-methyl-2-(i-propyl-1-oxoindan-5-ylacetamide is employed in the diethyl oxalate/potassium t-butoxide reaction there is obtained 4-[6,7-dichloro-2-methyl-2-(i-propyl)indan-2-on-5-yl]-3-hydroxy-3-pyrroline-2,5-dione. When 6,7-dichloro-2-ethyl-2-methyl-1-oxoindan-5-ylacetamide is utilized as starting material in this reaction there is obtained 4-(6,7-dichloro-2-ethyl-2-methylindan-1-on-5-yl)-3-hydroxy-3-pyrroline-2,5-dione. If 6,7-dichloro-2-ethyl-2-(n-propyl)-1-oxoindan-5-ylacetamide is the starting material, there is obtained 4-[6,7-dichloro-2-ethyl-2-(n-propyl)indan-1-on-5-yl]-3-hydroxy-3-pyrroline-2,5-dione.

When [6,7-dichloro-1-hydroxy-2-methyl-2-(i-propyl)-indan-5-yl]oxyacetamide is utilized as starting material in the reaction with diethyl oxalate/potassium t-butoxide there is obtained 4-[6,7-dichloro-1-hydroxy-2-methyl-2-(i-propyl)indan-5-yloxy]-3-hydroxy-3-pyrroline-2,5-dione. Where [6,7-dichloro-2-ethyl-1-hydroxy-2-(n-propyl)indan-5-yl]oxyacetamide is utilized as starting material in this reaction there is obtained 4-[6,7-dichloro-2-ethyl-1-hydroxy-2-(n-propyl)indan-5-yloxy]-3-hydroxy-3-pyrroline-2,5-dione.

When 6,7-dichloro-2,2-dimethyl-1-hydroxyindan-5-yloxyacetamide and 6,7-dichloro-2-methyl-2-(i-propyl)- pharmaceutically acceptable salts of formula (I) compounds. The compounds of formula (I) are strong organic acids with a pKa in the range 2–4. These salts are readily formed with the usual inorganic cations such as sodium, potassium and ammonium. Salts with organic amines such as trimethylamine, triethylamine, n-butylamine and the like are also very stable. The neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt.

The compounds of formula (I) are utilized for the stated utilities by formulating them in a composition such as tablet, capsule or elixir for oral administration. Sterile solutions or suspensions can be used for parenteral administration. About 10 to 200 mg of a compound of formula (I) or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose will be in the 30 to 2000 mg range with the preferred dosage range being 50 to 1000 mg.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose or lactose; a flavoring agent such as peppermint, oil of wintergreen or cherry. When the dosage unit form is a capsule, it may contain in addition to materials of the above type a liquid carrier such as a fatty oil. Various other materials may be present as coating or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

What is claimed is:

1. The compounds having the structure:

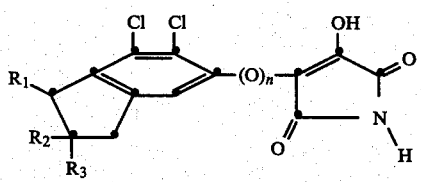

wherein
n is 0 or 1;
$R_1$ is —OH or =O;
$R_2$ is loweralkyl containing 1 to 3 carbons;
$R_3$ is loweralkyl containing 1 to 3 carbons cycloloweralkyl containing 4 to 6 carbons, with the proviso that when n is 1, $R_1$ is not =O or pharmaceutically acceptable salts thereof.

2. Compounds having the structure:

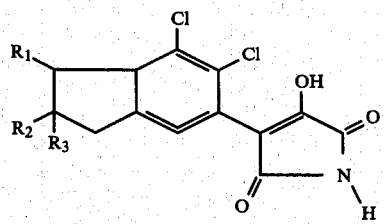

wherein
$R_1$ is —OH or =O;
$R_2$ is loweralkyl containing 1 to 3 carbons;
$R_3$ is loweralkyl containing 1 to 3 carbons, cycloloweralkyl containing 4 to 6 carbons or pharmaceutically acceptable salts thereof.

3. A compound of claim 2 designated 4-(6,7-dichloro-2-cyclopentyl-2-methylindan-1-on-5-yl)-3-hydroxy-3-pyrroline-2,5-dione.

4. Compounds having the structure

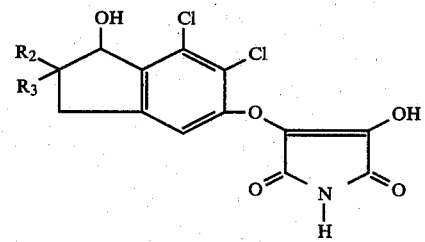

wherein
$R_2$ is loweralkyl containing 1 to 3 carbons;
$R_3$ is loweralkyl containing 1 to 3 carbons, cycloloweralkyl containing 4 to 6 carbons or pharmaceutically acceptable salts thereof.

5. A compound of claim 4 designated 4-(6,7-dichloro-2-cyclopentyl-1-hydroxy-2-methylindan-5-yloxy)-3-hydroxy-3-pyrroline-2,5-dione.

6. A pharmaceutical composition useful in the treatment and prevention of calcium oxalate kidney and bladder stone formation comprising an effective amount of a compound of claim 1 or the pharmaceutically acceptable salts thereof and a pharmaceutically acceptable carrier thereof.

7. A pharmaceutical composition useful in the treatment and prevention of calcium oxalate kidney and bladder stone formation comprising an effective amount of 4-(6,7-dichloro-2-cyclopentyl-2-methylindan-1-on-5-yl)-3-hydroxy-3-pyrroline-2,5-dione or the pharmaceutically acceptable salts thereof and a pharmaceutically effective carrier therefor.

8. A pharmaceutical composition useful in the treatment and prevention of calcium oxalate kidney and bladder stone formation comprising an effective amount of 4-(6,7-dichloro-2-cyclopentyl-1-hydroxy-2-methylindan-5-yloxy)-3-hydroxy-3-pyrroline-2,5-dione or the pharmaceutically acceptable salts thereof and a pharmaceutically effective carrier therefor.

9. A method of treating persons afflicted with calcium oxalate kidney or bladder stones or preventing the formation of calcium oxalate kidney or bladder stones which comprises administering to such a patient an effective amount of a compound of claim 1.

10. A method of treating persons afflicted with calcium oxalate kidney or bladder stones, or preventing the formation of kidney or bladder stones, which comprises administering to such a patient an effective amount of 4-(6,7-dichloro-2-cyclopentyl-2-methylindan-1-on-5-yl)-3-hydroxy-3-pyrroline-2,5-dione.

11. A method of treating persons afflicted with calcium oxalate kidney or bladder stones, or preventing the formation of kidney or bladder stones, which comprises administering to such a patient an 4-(6,7-dichloro-2-cyclopentyl-1-hydroxy-2-methylindan-5-yloxy)-3-hydroxy-3-pyrroline-2,5-dione.

* * * * *